United States Patent
Vasseur-Demarcy et al.

(10) Patent No.: US 10,675,271 B2
(45) Date of Patent: Jun. 9, 2020

(54) CLONIDINE AND/OR CLONIDINE DERIVATIVES FOR USE IN THE PREVENTION AND/OR TREATMENT OF ADVERSE SIDE EFFECTS OF CHEMOTHERAPY

(71) Applicant: ONXEO, Paris (FR)

(72) Inventors: Bérangère Vasseur-Demarcy, Deuil la Barre (FR); Pierre Attali, Vincennes (FR)

(73) Assignee: MONOPAR THERAPEUTICS, INC., Wilmette, IL (US)

( * ) Notice: Subject to any disclaimer, the term of this patent is extended or adjusted under 35 U.S.C. 154(b) by 127 days.

(21) Appl. No.: 15/566,775

(22) PCT Filed: Apr. 17, 2015

(86) PCT No.: PCT/EP2015/058419
§ 371 (c)(1),
(2) Date: Oct. 16, 2017

(87) PCT Pub. No.: WO2016/165775
PCT Pub. Date: Oct. 20, 2016

(65) Prior Publication Data
US 2018/0098966 A1    Apr. 12, 2018

(51) Int. Cl.
*A61K 45/06* (2006.01)
*C07C 25/08* (2006.01)
*A61K 31/4168* (2006.01)

(52) U.S. Cl.
CPC .......... *A61K 31/4168* (2013.01); *A61K 45/06* (2013.01); *C07C 25/08* (2013.01); *A61K 2300/00* (2013.01)

(58) Field of Classification Search
CPC ................ A61K 31/4168; A61K 45/06; A61K 2300/00; C07C 25/08
USPC ....................................................... 514/392
See application file for complete search history.

(56) References Cited

U.S. PATENT DOCUMENTS 8,198,264 B2 *  6/2012  Tahara ............... A61K 31/7072
                                                      514/183
2002/0045565 A1    4/2002  Robichaud 2004/0101582 A1   5/2004  Wolicki
2005/0059744 A1   3/2005  Donello et al.
2013/0168375 A1   7/2013  Aberg

FOREIGN PATENT DOCUMENTS

| EP | 0043659 A1 | 1/1982 |
|---|---|---|
| EP | 0542824 A1 | 5/1993 |
| EP | 1972332 A1 | 9/2008 |
| EP | 2165706 A1 | 3/2010 |
| EP | 2368549 A1 | 9/2011 |
| JP | 2007-505113 A | 3/2007 |
| JP | 57-40470 B2 | 6/2015 |
| WO | WO-2006/063446 A1 | 6/2006 |
| WO | WO-2007/017571 A1 | 2/2007 |
| WO | WO-2010/031819 A1 | 3/2010 |

OTHER PUBLICATIONS

International Search Report and Written Opinion, International Application No. PCT/EP2015/058419, dated Jun. 23, 2015.
Le et al., Palifermin reduces severe mucositis in definitive chemoradiotherapy of locally advanced head and neck cancer: a randomized, placebo-controlled study, J. Clin. Oncol., 29(20):2808-14 (2011).
Roila et al., Guideline update for MASCC and ESMO in the prevention of chemotherapy- and radiotherapy-induced nausea and vomiting: results of the Perugia consensus conference, Ann. Oncol., 21 Suppl 5:v232-43 (2010).
Astolfi et al., Correlation of adverse effects of cisplatin administration in patients affected by solid tumours: a retrospective evaluation, Oncol. Rep. 29(4):1285-92 (Apr. 2013).
Yoshikawa et al., Management of cancer-related fatigue, Japanese Journal of Pharmaceutical Palliative Care and Sciences, vol. 7, pp. 1-6 (2014).
Japanese Patent Application No. 2017-554373, Notice of Reasons for Rejection, dated Feb. 6, 2019.

* cited by examiner

*Primary Examiner* — Yevgeny Valenrod
(74) *Attorney, Agent, or Firm* — Marshall, Gerstein & Borun LLP

(57) ABSTRACT

The present invention pertains to specific clonidine and/or clonidine derivatives for use in the prevention and/or treatment of adverse side effects of alkylating agent chemotherapy, other than those resulting from mucosal inflammation. It also pertains to the use of this clonidine and/or clonidine derivative for the manufacture of a pharmaceutical composition intended to prevent and/or alleviate the adverse side effects of alkylating agent chemotherapy, other than those resulting from mucosal inflammation. This invention is further directed to a kit comprising: (a) a clonidine and/or clonidine derivative, and (b) at least one alkylating chemotherapeutic agent, as a combined preparation for simultaneous, separate or sequential use in the treatment of cancer.

12 Claims, No Drawings

CLONIDINE AND/OR CLONIDINE DERIVATIVES FOR USE IN THE PREVENTION AND/OR TREATMENT OF ADVERSE SIDE EFFECTS OF CHEMOTHERAPY

FIELD OF THE INVENTION

The present invention pertains to the prevention and/or treatment of adverse side effects of chemotherapy, other than those resulting from mucosal inflammation.

BACKGROUND OF THE INVENTION

Chemotherapy has been widely used to administer cytostatic and antineoplastic agents to patients suffering from cancer. Although chemotherapy is efficient against some cancers, it is often exhausting for patients. Moreover, current chemotherapeutic agents have a number of adverse side effects due to their non-specific cytotoxicity, which usually affect not only tumor cells, but also normal cells having a high mitotic activity, such as epithelial cells. This is especially the case with alkylating agents, which are used in approximately half of all chemotherapy treatments to inhibit DNA replication of cancerous cells. Non-alkylating cancer chemotherapy drugs are also toxic to mammalian cells; they can inhibit multiple sites within a replicating cell, such as synthesis of nucleotides required for DNA replication and microtubule function required for mitosis.

Non limiting examples of non-alkylating cancer chemotherapy drugs and their adverse side effects are given below.
  Classical Alkylating Agents
  Many of the agents are known as "Classical alkylating agents". These include alkyl groups, and have been known for a longer time than some of the other alkylating agents. Examples include melphalan and chlorambucil. They destroy proliferating cancer cells by adding an alkyl group to DNA molecule and preventing its replication.
  The following three groups are almost always considered "classical".
    Nitrogen mustards, like: Cyclophosphamide, Mechlorethamine or mustine (HN2) (trade name Mustargen), Uramustine or uracil mustard, Melphalan, Chlorambucil, Ifosfamide, Bendamustine, . . .
    Nitrosoureas, like: Carmustine, Lomustine, Streptozocin, . . .
    Alkyl sulfonates like: Busulfan, Thiotepa, . . .
  Alkylating-Like Agents
  Platinum-based chemotherapeutic drugs (termed platinum analogues) act in a similar manner. These agents do not have an alkyl group, but nevertheless damage DNA. They permanently coordinate to DNA to interfere with DNA repair, so they are described as "alkylating-like". Some non limiting example of platinum analogues are: Platinum, Cisplatin, Carboplatin, Nedaplatin, Oxaliplatin, Satraplatin, Triplatin tetranitrate, . . .
The alkylating agents all have numerous adverse side effects, but the predominant toxicities are on gastrointestinal tract (vomiting, nausea, diarrhea) and mucositis, a severe inflammation of the mucosa.

The toxicity of cancer therapy for epithelial cells accounts for many of the side effects commonly suffered by persons undergoing a regimen of chemotherapy. These complications can be so difficult to endure that it is not uncommon for patients to forego or discontinue recommended cancer therapy treatments.

Most common complications of chemotherapy include nausea, vomiting, diarrhea or constipation, asthenia, fatigue, mucositis, alopecia, respiratory and cognitive disorders. Toxicity against various cells including blood cells, hepatic cells, nerve cells, lung cells and heart cells has also been reported. Blood cell poisoning may result in anemia and depression of the immune system leading to infections. Nerve cell damage may cause headache, inter alia, whereas lung cell poisoning typically results in coughing spells. To date, prophylactic treatments have been provided in order to reduce the severity or occurrence of some of the above adverse side effects. For instance, erythropoietin (EPO) is recommended to prevent anemia and granulocytic growth factors (GCSF) to boost the immune system. However, vomiting and nausea continue to be the most distressing side effects of cancer chemotherapy. They may ultimately result in weight loss, which is another adverse event associated with chemotherapy that may compromise a patient's chances of recovery, because his ability to fight disease may be reduced by a weakened state. It has especially been reported that platinum-based chemotherapy, and notably cisplatin has the highest emetogenicity effect among antineoplastic agents (*Annals of Oncology*, 21 (Supplement 5): v232-v243, 2010). To prevent acute nausea and vomiting, an anti-emetic drug regimen is recommended, including a 5-HT3 receptor antagonist and/or dexamethasone and/or aprepitant, which is a selective antagonist of the neurokinin $(NK)_1$ neurotransmitter receptor. Although these prophylactic treatments have proven to be rather efficient on vomiting, identification of anti-nausea agents remains a big challenge.

Moreover, chemotherapy is frequently administered concurrently with radiotherapy, which shares with chemotherapy several of the above adverse events, such as nausea and vomiting, asthenia, headache and cough. This is because radiation therapy achieves most of its cell killing properties by generating oxygen radicals within cells, which may also kill mammalian cells.

It would therefore be particularly useful to provide a single prophylactic treatment that would be efficient against many of these adverse side effects of chemotherapy, in order to avoid treating each of the above conditions separately.

SUMMARY OF THE INVENTION

Clonidine and/or Clonidine derivatives are well known drugs for treating hypertension. Applicant has also described for the first time that Clonidine and/or Clonidine derivatives are efficient for treating mucositis, a specific adverse side effect of radiotherapy and chemotherapy based on alkylating agents (WO 2010/031819). Mucositis is an inflammatory disorder affecting oral or gastro-intestinal mucosa and a frequent complication of face and neck radiotherapy.

The Applicant has now surprisingly found that administering a clonidine derivative to patients before, during or after alkylating agents chemotherapy is an efficient way to prevent and/or alleviate many other chemotherapy adverse side effects of alkylating agents.

It was fully unpredictable that clonidine and/or clonidine derivatives could efficiently prevent and/or alleviate adverse side effects of alkylating agents chemotherapy, other than those resulting from mucosal inflammation (like mucositis). On the contrary, it was suggested in WO 2010/031819 to add antiemetic drugs to the compositions containing clonidine derivatives, in order to treat nausea and vomiting.

Moreover, the only active agent currently marketed for the treatment of oral mucositis, i.e. palifermin, was shown to have no effect against nausea, vomiting, fatigue and related weight loss (Quynh-Thu Le et al., *Journal of Clinical Oncology*, Vol. 29, No 20, Jul. 10, 2011).

Hence, the inventors have unexpectedly shown that clonidine and/or clonidine derivatives are able to alleviate many adverse side effects of alkylating agents chemotherapy, other than those resulting from mucosal inflammation (like mucositis). Among adverse side effects of chemotherapy based on alkylating agents, clonidine and/or clonidine derivatives have shown particular prevention and/or treatment of gastrointestinal disorder (vomiting, nausea, diarrhea), respiratory disorders, fatigue, asthenia and headache.

Thus, this invention is directed to a clonidine and/or clonidine derivative selected from compounds of the following formula (I):

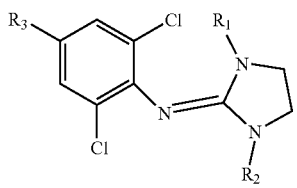

wherein:
$R_1$ and $R_2$ are independently selected from H and —OCOR, and
$R_3$ is selected from H, —CH$_2$OH, —OCOR, —COOR, —NH$_2$, —NHR, —NRR' and —NHCOR,
wherein R and R' independently designate a linear or branched alkyl group having from 1 to 6 carbon atoms, which may be substituted by one or more groups selected from a halogen atom, an amino group and an alkylamino group which alkyl part is a linear or branched alkyl having from 1 to 6 carbon atoms,
and tautomer forms and pharmaceutically acceptable salts thereof,
for use in the prevention and/or treatment of adverse side effects of alkylating agent chemotherapy, other than those resulting from mucosal inflammation.

This invention is also directed to the use of a clonidine and/or clonidine derivative as mentioned above for the manufacture of a pharmaceutical composition intended to prevent and/or treat the adverse side effects of alkylating agent chemotherapy, other than those resulting from mucosal inflammation.

It further pertains to a method for preventing and/or treating the adverse side effects of alkylating agent chemotherapy, other than those resulting from mucosal inflammation, comprising the step consisting of administering, to a subject in need thereof, an effective amount of a clonidine and/or clonidine derivative as defined above, thereby preventing and/or alleviating said adverse side effects.

This invention is also directed to a kit comprising: (a) clonidine and/or a clonidine derivative as described above, and (b) at least one alkylating chemotherapeutic agent, as a combined preparation for simultaneous, separate or sequential use in the treatment of cancer.

DETAILED DESCRIPTION

This invention is directed to clonidine and/or a clonidine derivative comprising compounds of formula (I) and tautomer forms and pharmaceutically acceptable salts thereof, for use in the prevention and/or treatment of adverse side effects of chemotherapy based on alkylating agent (also herein named "alkylating agent chemotherapy"), other than those resulting from mucosal inflammation.

"Prevention" as used herein means that treatment is started prior to chemotherapy and hinders the onset of the adverse side effects resulting therefrom.

"Treatment" as used herein means that once a mammal has developed at least one symptom or adverse side effect in the course of chemotherapy, further progress of this adverse side effect is slowed down and/or this adverse side effect is alleviated.

The term "adverse side effect" or "adverse event" is defined as any unfavorable and unintended sign, symptom or disease associated with chemotherapy, including underlying conditions which become aggravated during chemotherapy. Adverse side effects are usually evaluated using the NCI Common Terminology Criteria for Adverse Events, version 3.0. If not listed therein, they may be classified from mild (usually transient in nature, not interfering with normal activities and not requiring any treatment) to moderate (sufficiently discomforting to interfere with normal activities but requiring no or minimal treatment) and severe (preventing normal activities and requiring assistance or therapy).

The adverse side effects which are prevented or treated according to this invention include:
gastrointestinal disorders, especially nausea, vomiting and/or diarrhea,
respiratory disorders such as cough,
asthenia and/or fatigue,
headache.

Among compounds of formula (I), mention can be made, for instance, of those selected from the group consisting of: clonidine, p-aminoclonidine, p-diethylamino clonidine, p-ethylamino clonidine, p-acetamido clonidine, p-bromoacetamido clonidine, p-N-chloroethyl-N-methylamino clonidine, p-N-β-chloroethyl-N-methylaminomethyl clonidine, 3,5-dichloro-4-(imidazolidin-2-ylideneamino)benzyl alcohol, 3,5-dichloro-4-(1,3-diisobutyryl imidazolidin-2-ylideneamino)benzyl isobutyrate, ethyl 3,5-dichloro-4-(1-isobutyrylimidazolidin-2-ylideneamino)benzoate, and mixtures thereof.

An example of pharmaceutically acceptable salt of the compounds of formula (I) include their hydrochloride salt.

Clonidine ($R_1$=$R_2$=$R_3$=H in formula (I) above) and pharmaceutically acceptable salts thereof are particularly preferred. Clonidine hydrochloride is pharmaceutically acceptable salt particularly preferred according to this invention.

As mentioned above, the clonidine and/or clonidine derivatives of this invention also encompass tautomer forms of the compounds of formula (I). For example, not intended as a limitation, tautomers are possible between the 4,5-dihydrooxazole and the adjacent nitrogen as shown below:

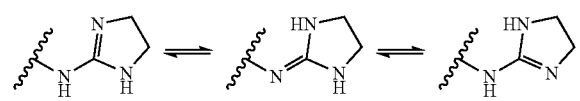

The clonidine and/or clonidine derivatives may be administered to a subject before, simultaneously with, and/or after chemotherapy based on alkylating agents. They are typically used in a pharmaceutically effective amount, which means that they are administered in an amount sufficient to achieve at least partially the desired effect. In this regard, it has been shown that a daily oral intake of 20 to 150 µg, and preferably from 50 to 100 µg, of clonidine and/or clonidine derivative (expressed as base equivalent) efficiently reduces the risk of occurrence of adverse side effects and/or the intensity of the symptoms. This daily amount of clonidine and/or clonidine derivative may be administered in a single dose or in two divided doses, preferably in a single dose. According to a preferred embodiment of this invention, a single daily dose of 50 µg of clonidine and/or clonidine derivative is administered to the patient for a duration of, e.g., from 6 to 10 weeks, preferably during 8 weeks.

The compounds of this invention may be useful for preventing and/or treating the above adverse effects resulting from any kind of alkylating agent chemotherapeutic treatment. Among these agents, mention can especially be made of platinum derivatives. This invention thus applies in a preferred embodiment to platinum-based chemotherapy, which may be selected from cisplatin chemotherapy, carboplatin chemotherapy and oxaliplatin chemotherapy, preferably cisplatin chemotherapy.

According to an embodiment of this invention, the patient is further treated with radiotherapy during the course of the alkylating agent chemotherapeutic treatment. The clonidine and/or clonidine derivative as described above is thus used in an alkylating agent chemotherapeutic treatment as described herein in combination with radiotherapy. In such a case, the clonidine and/or clonidine derivative may be administered on a daily basis to the patient, starting from 1 to 8 days, preferably from 1 to 3 days, before radiotherapy, until the end of radiotherapy and/or for a duration of from 6 to 10 weeks, for instance 8 weeks.

The clonidine and/or clonidine derivatives may be included in a pharmaceutical composition comprising a pharmaceutically acceptable carrier. This carrier may be in a solid or liquid form, for instance. Solid carriers comprise powders, granules, capsules, tablets, films and the like. Liquid carriers may be water-based, oil-based or in the form of a water-in-oil or oil-in-water emulsion or dispersion, for instance.

The pharmaceutical composition containing the clonidine and/or clonidine derivative can be administered in any form such as orally, topically, parenterally, intranasally, transmucosally, and the like. According to a preferred embodiment of this invention, this composition is suitable for transmucosal administration. In this embodiment, the clonidine derivative may be formulated in a mucoadhesive buccal tablet, that can have any shape such as rectangular, circular, square, oval and the like.

Moreover, it is preferred that the composition of this invention provides sustained release of clonidine and/or clonidine derivative. The sustained release is for a period of at least 4 hours and preferably from 4 to 25 hours.

This mucoadhesive tablet comprises or consists essentially of (i.e. includes at least 90% by weight) at least clonidine and/or one clonidine derivative as the active ingredient, at least one diluent, at least one bioadhesive agent and preferably at least one sustained release agent and/or at least one binder.

The diluent used in the present invention can be insoluble or soluble. Examples of diluents include microcrystalline cellulose, silicified microcrystalline cellulose, hydroxypropyl methylcellulose, dibasic calcium phosphate, calcium carbonate, calcium sulfate, magnesium carbonate, mannitol, glucose, sorbitol, dextrose, lactose, starch and the like.

The diluent is usually present in an amount between 1 and 75% by weight, preferably between 10% to 60% by weight and more preferably from 20 to 40% by weight, based on the total weight of the mucoadhesive tablet.

The bioadhesive agent is usually a synthetic or a natural protein or a polysaccharide.

The natural protein can be of vegetal or animal origin. The proteins of vegetal origin that can be used are those described in EP 1 972 332. Examples of these proteins include natural pea proteins, natural wheat proteins and gliadin proteins and mixtures thereof. The method for producing pea proteins is described in, e.g., WO 2007/017571. In another embodiment, the natural proteins of animal origin that can be used are those described in EP 0 542 824. A particular example is a milk protein concentrate titrating a minimum of 85% of proteins such as Prosobel L85, milk protein concentrate or, preferably, either Promilk 852A sold by Armor Proteins, or from the Alaplex range (4850, 1180, 1380 or 1395) sold by NZMP. The relative concentration of the milk natural proteins in the mucoadhesive tablet of the invention preferably ranges from 15% to 50% by weight, preferably from 20% to 30% by weight.

The polysaccharide that can be used in the present invention includes chitosan, alginate, carboxymethyl cellulose, hydroxypropyl methyl cellulose, hydroxyethyl cellulose, hydroxypropyl cellulose, cyclodextrin, sodium hyaluronate and xanthan gum.

The binder can be selected from carboxyvinyl polymers, carmellose, methylcellulose, hydroxyethylcellulose, hydroxypropylcellulose, hydroxymethylcellulose, hydroxyethylmethyl cellulose, polyvinylpyrrolidone (povidone), polyvinyl alcohol, and the like. The binders may be present in the amount of 0.5 to 5% by weight, based on the total weight of the mucoadhesive tablet.

In the case where it is designed for sustained release of the clonidine derivative, the mucoadhesive tablet comprises a sustained release agent which may include hydrophilic polymers including polysaccharides such as cellulose based polymers such as hypromellose, cellulose acetate, cellulose esters, cellobiose or cellulose resins; a carboxyvinyl polymer such as Carbopol 934®; hydroxyethylmethacrylate; and mixtures thereof. Other polymers that can be used in the present invention include cellulose ethers, xanthan gum, scleroglucan, locust bean gum, gum Arabic, gum tragacanth, carob, alginic acid, alginates, carrageenanes, agar-agar, starch, and guar gum, either alone or in mixtures thereof.

The sustained release agents are generally present in a concentration of 5% to 80% by weight, preferably from 10% to 60% by weight and more preferably from 20 to 40% by weight, based on the total weight of the mucoadhesive tablet.

The mucoadhesive tablet may also comprise at least one additive selected from the group consisting of a glidant, a lubricant, a coloring agent, a flavouring agent, a wetting agent and mixtures thereof.

Flavoring agents include flavors, calcium citrate, Safrole, and sweetening agents such as aspartame, cyclamates, saccharin and xylitol. Additionally, glidants may be selected from talc and colloidal silicon dioxide, and lubricants may include magnesium stearate, stearic acid and polyethylene glycol. The wetting agent can be a water solution or a solvent such as an alcohol. These additional agents can be added to the carrier in the concentration range of 0.1 to 10% by weight, relative to the total weight of the mucoadhesive tablet.

According to a preferred embodiment of this invention, the pharmaceutical composition comprising clonidine and/or clonidine derivative as described above includes all the following excipients:
water as a wetting agent,
a diluent such as microcrystalline cellulose,
a binder such as polyvinylpyrrolidone (povidone),
a sustained release agent such as hydroxypropyl methylcellulose (hypromellose),
a milk protein concentrate,
a glidant such as colloidal silicon dioxide, and
a lubricant such as magnesium stearate.

In the case where the pharmaceutical composition comprising clonidine and/or a clonidine derivative of this invention is applied as a mucoadhesive buccal tablet, the latter may be adhered to a gum (preferably to the upper gum, for instance just above the incisor tooth) and a slight pressure exerted thereon so as to maintain the same in place. The tablet is preferably applied after cleaning the teeth. A sustained release of clonidine derivative in the mouth may thus be attained.

According to one embodiment of this invention, the composition comprising clonidine and/or a clonidine derivative as described above may further include at least one chemotherapeutic agent.

In an alternative embodiment, a kit may be provided, comprising: (a) clonidine and/or a clonidine derivative as described above, and (b) at least one chemotherapeutic agent, as a combined preparation for simultaneous, separate or sequential use in the treatment of cancer. This kit usually contains two different compositions, one of which includes the clonidine derivative and the other of which includes one or several chemotherapeutic agents. These two compositions may be administered by the same route or via different routes.

EXAMPLES

This invention will be better understood in light of the following examples which are given for illustrative purposes only and do not intend to limit the scope of the invention, which is defined by the attached claims.

Example 1: Preparation of Mucoadhesive Tablets of Clonidine Hydrochloride

1A—Tablet Containing 0.1 mg Clonidine 0.1 mg (base equivalent) of clonidine hydrochloride was blended with 13 mg of dibasic calcium phosphate, 15 mg of microcrystalline cellulose, 40 mg of hydroxypropyl methylcellulose, 1 mg of colloidal silica and 0.9 mg of magnesium stearate.

The mixture was then homogenized by sieving and 30 mg of milk protein concentrate was added and mixed with the initial mixture. The resulting composition was then compressed under sufficient pressure to form a tablet.

1B—Tablets Containing 0.05 and 0.1 mg Clonidine

An aqueous solution of clonidine hydrochloride was sprayed on a mixture composed of microcrystalline cellulose, milk protein concentrate and povidone. Granulation continued until enough cohesion of the powders was obtained. After drying and sieving, hydroxypropyl methyl cellulose was added to the granules and mixed until blend uniformity was obtained. Finally, magnesium stearate was added and mixed with the final blend. The resulting composition was then compressed under sufficient pressure to form a tablet.

1C—Tablets Containing 0.05 and 0.1 mg Clonidine

An aqueous solution of clonidine hydrochloride was sprayed on a mixture composed of microcrystalline cellulose and povidone. Granulation continued until enough cohesion of the powders was obtained. After drying and sieving, hydroxypropyl methyl cellulose, colloidal silica, talc and milk protein concentrate were added to the granules and mixed until blend uniformity was obtained. Finally, magnesium stearate was added and mixed with the final blend. The resulting composition was then compressed under sufficient pressure to form a tablet.

1D—Tablets Containing 0.05 mg Clonidine

An aqueous solution of clonidine hydrochloride was mixed with povidone. Microcrystalline cellulose and a milk protein concentrate were then added to this mixture and the resulting blend was granulated, dried and sieved. Hypromellose and colloidal silicon dioxide were then added to this powder in order to obtain a final blend to which magnesium stearate was added as a lubricant. The resulting composition was then compressed under sufficient pressure to form a tablet.

Example 2: Preventive Treatment of Adverse Effects of Chemotherapy

A phase II, multicentre, randomised, double-blind, placebo-controlled study was performed to compare the efficacy of the mucoadhesive buccal tablets of Example 1D, comprising 50 µg of clonidine hydrochloride, applied once daily to that of placebo in the prevention and treatment of skin injury following radiotherapy in patients with head and neck cancer (suffering from a newly diagnosed squamous cell carcinoma of the oral cavity, oropharynx, hypopharynx or larynx). These patients received, within 15 weeks after curative surgery, a cumulative radiation dose of radiation ranging from 50 to 70 Gray in oral cavity, based on a daily dosing between 1.8 and 2.2 Gy, combined with platinum-based chemotherapy, based on a weekly or tri-weekly cycle. Clonidine was administered in the form of a mucoadhesive tablet that was applied into the mouth, on the upper gum, for about 30 seconds, after which it remained in place for several hours. The treatment with clonidine hydrochloride started from 1 to 3 days before radiotherapy until the end of radiotherapy, for up to 8 weeks. Patients were evaluated twice a week during the radiotherapy period, then one month after stop of radiotherapy.

The following adverse side effects were reported for the treated group and the placebo group.

|  | Nausea | Vomiting | Diarrhoea | Asthenia | Fatigue | Cough | Headache |
| --- | --- | --- | --- | --- | --- | --- | --- |
| Placebo | 71.0% | 38.7% | 21.0% | 24.2% | 12.9% | 12.9% | 14.5% |
| Clonidine | 52.7% | 25.5% | 12.7% | 16.4% | 9.1% | 5.5% | 9.1% |

Moreover, an additional experiment identical to the above one but using 100 μg of clonidine hydrochloride resulted in an even decreased occurrence of nausea (46.9%).

This example demonstrates that the clonidine derivatives of this invention efficiently decrease the occurrence of the adverse side effects of chemotherapy.

The invention claimed is:

1. A method for treating asthenia and/or fatigue due to alkylating agent chemotherapy comprising administering to a subject in need thereof a clonidine and/or clonidine derivative selected from compounds having the following formula (1).

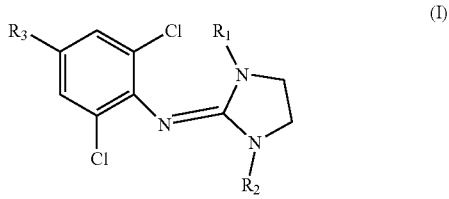

(I)

wherein:

$R_1$ and $R_2$ are independently selected from H and —OCOR, and $R_3$ is selected from H, —CH2OH, —OCOR, —COOR, —NI, —NHR, —NRR' and —NHCOR, wherein R and R' independently designate a linear or branched alkyl group having from 1 to 6 carbon atoms, which may be substituted by one or more groups selected from a halogen atom, an amino group and an alkylamino group which alkyl part is a linear or branched alkyl having from 1 to 6 carbon atoms, and tautomer forms and pharmaceutically acceptable salts thereof.

2. The method of claim 1 wherein the alkylating agent chemotherapy is a platinum-based chemotherapy selected from the group consisting of, cisplatin, carboplatin and oxaliplatin.

3. The method of claim 1 wherein the clonidine and/or clonidine derivative is administered to a subject before, simultaneously with, and/or after chemotherapy.

4. The method of claim 1 wherein the clonidine and/or clonidine derivative claim 1 is administered to a subject having a head and neck cancer.

5. The method of claim 1, wherein the compound of formula (1) is selected from the group consisting of: clonidine, p-aminoclonidine, p-diethylamino clonidine, p-ethylamino clonidine, p-acetamido clonidine, p-bromoacetamido clonidine, p-N-chloroethyl-N-methylamino clonidine, p-N-β-chloroethyl-N-methylaminomethyl clonidine, 3,5-dichloro-4-(imidazolidin-2-ylideneamino)benzyl alcohol, 3,5-dichloro-4-(1,3-diisobutyryl imidazolidin-2-ylideneamino) benzyl isobutyrate, ethyl 3,5-dichloro-4-(1-isobutyryl imidazolidin-2-ylideneamino)benzoate, and mixtures thereof.

6. The method of claim 1 wherein the clonidine and/or clonidine derivative is selected from clonidine and pharmaceutically acceptable salts thereof, particularly clonidine hydrochloride.

7. The method of claim 1, wherein the clonidine and/or clonidine derivative is included in a pharmaceutical composition comprising a pharmaceutically acceptable carrier.

8. The method of claim 7, wherein said composition is suitable for transmucosal administration.

9. The method of claim 8, wherein said composition provides for sustained release of the clonidine derivative.

10. The method of claim 1, wherein the clonidine and/or clonidine derivative is administered on a daily basis, with a daily oral intake of clonidine derivative ranging from 20 to 150 μg, and preferably from 50 to 100 μg.

11. The method of claim 1, wherein the clonidine and/or clonidine derivative is administered in combination with radiotherapy.

12. The method of claim 1, wherein the clonidine derivative is administered on a daily basis to the patient, starting from 1 to 8 days, preferably from 1 to 3 days, before radiotherapy, until the end of radiotherapy and/or for a duration of from 6 to 10 weeks, for instance 8 weeks.

* * * * *